(12) United States Patent
Laurino

(10) Patent No.: US 10,858,467 B2
(45) Date of Patent: *Dec. 8, 2020

(54) CONDUCTING POLYMER, 1-OCTADECENE, POLYMER WITH 2,5 FURNADIONE, METAL SALTS

(71) Applicant: Joseph Laurino, Ft. Lauderdale, FL (US)

(72) Inventor: Joseph Laurino, Ft. Lauderdale, FL (US)

(*) Notice: Subject to any disclaimer, the term of this patent is extended or adjusted under 35 U.S.C. 154(b) by 243 days.

This patent is subject to a terminal disclaimer.

(21) Appl. No.: 14/064,827

(22) Filed: Oct. 28, 2013

(65) Prior Publication Data

US 2015/0119529 A1    Apr. 30, 2015

(51) Int. Cl.
| | | |
|---|---|---|
| *C08F 222/02* | (2006.01) | |
| *H01B 1/12* | (2006.01) | |
| *C08F 8/44* | (2006.01) | |
| *C08F 10/14* | (2006.01) | |
| *C08F 222/04* | (2006.01) | |
| *C08F 222/06* | (2006.01) | |

(Continued)

(52) U.S. Cl.
CPC ............ *C08F 222/02* (2013.01); *C08F 8/44* (2013.01); *C08F 10/14* (2013.01); *C08F 222/04* (2013.01); *C08F 222/06* (2013.01); *C08F 222/14* (2013.01); *H01B 1/125* (2013.01); *C08F 8/12* (2013.01); *C08F 8/14* (2013.01); *C08F 22/02* (2013.01); *C08F 22/04* (2013.01); *C08F 22/06* (2013.01); *C08F 122/02* (2013.01)

(58) Field of Classification Search
CPC .......... C08F 22/02; C08F 22/04; C08F 22/06; C08F 222/02; C08F 222/04; C08F 222/06; C08F 222/14; C08F 18/14

See application file for complete search history.

(56) References Cited

U.S. PATENT DOCUMENTS

| | | | | |
|---|---|---|---|---|
| 6,203,727 B1* | 3/2001 | Babinec | ............... | C08G 61/122 252/500 |
| 6,214,972 B1* | 4/2001 | Abramovitz | ........... | C07K 14/72 435/252.3 |

(Continued)

FOREIGN PATENT DOCUMENTS

| | | | | |
|---|---|---|---|---|
| DE | 3336129 A1 * | 4/1985 | ............. | B01D 71/76 |
| JP | 2003295380 A | * 10/2003 | | |

OTHER PUBLICATIONS

The Book and Paper Group Annual; vol. 3, 1984; Sulubility Parameters; Theroy and Application; John Burke.

(Continued)

*Primary Examiner* — Ling Siu Choi
*Assistant Examiner* — David L Miller
(74) *Attorney, Agent, or Firm* — Edward P Dutkiewicz

(57) ABSTRACT

A Polymer having an acid number greater than 100. The Polymer has a valent metal ion which is bonded to at least one reactive group. The characteristics of the Polymer include, conductivities of 4 S/cm to 200 S/cm or more, depending upon the concentration and nature of the metal bound. The conductivity proportional to the amount of metal bound, the ability of the Polymer to bind metals having a +1, +2, +3, +4, or +5 valence charge to the Polymer, and the ability to bind two or more different metals to separate binding sites on the Polymer.

2 Claims, 2 Drawing Sheets

(51) Int. Cl.
*C08F 222/14* (2006.01)
*C08F 8/12* (2006.01)
*C08F 122/02* (2006.01)
*C08F 8/14* (2006.01)
*C08F 22/02* (2006.01)
*C08F 22/06* (2006.01)
*C08F 22/04* (2006.01)

(56) References Cited

U.S. PATENT DOCUMENTS

| | | |
|---|---|---|
| 7,964,688 B2 | 6/2011 | Laurino |
| 8,420,757 B1 | 4/2013 | Laurino |
| 8,519,075 B2 | 8/2013 | Laurino |
| 2009/0139929 A1* | 6/2009 | Laurino ............ B01J 45/00 210/638 |
| 2010/0222542 A1* | 9/2010 | Laurino ............ B01J 45/00 528/196 |
| 2010/0311938 A1* | 12/2010 | Laurino ............ B01J 45/00 528/272 |
| 2011/0260111 A1* | 10/2011 | Nie ............ B82Y 10/00 252/301.36 |

OTHER PUBLICATIONS

Supp.A; Fried, Jr., Introduction to Polymer Science, Chapter 1, Polyme Science and Technology, 3rd Edition, Prentice Hall, NJ., US, (c) 2014, ISBN—13:978-0-13-703955-5.

Supp.B:Komber, H., The H and C NMR spectra of alternating isobutene/maleic an hydride copolymer,Macromol.Chem.Phys. 197, 343-353(1996).

Supp.C. C.C. Reichhardt and T. Welton. Solvents and Solvent Effects in Orgainc Chemistry, 4th Ed. J. Wiley-VCH Pub. Co. US (C)2011, ISBN:978-3-527-32473-6, p. 66.

Supp.D. Selected Values of Electric Dipole Moments for Molecules in the Gas Phase, Handbook of Chemistry and Physics, 54th Ed, 1973-1974, CRC Pres, US, A Taylor & Francis Group, (C) 1974, p. E-64.

Yaws, C.L; Narasimhan, P.K., Dipole Moment-Organic Compounds, In; Thermophysical Properties of Chemicals and Hydrocarbons, Chapter 19. William Andrew Publishing; © 2009 pp. 672-682. ISBN 978081551968 scet.bvtanel @ p. 675.

Supplement C; C.C. Reichhardt & T.Welton; Solvents and Solvent Effects in Orgainic Chemistry 4th ed.; J.Wiley-VCH Pub Co. US 2011; ISBN 978-3-527-32473-6; p. 66.

Supplemental Material F; ASTM 3644-15; Standard Test Method for Acid Number of Styrene-Maleic Anhydride Resins; ASTM International, 2019.

* cited by examiner

CONDUCTING POLYMER, 1-OCTADECENE, POLYMER WITH 2,5 FURNADIONE, METAL SALTS

RELATED PATENT APPLICATIONS

There are no related patent applications.

BACKGROUND OF THE INVENTION

Field of the Invention

The present invention relates to 1-OCTADECENE, POLYMER WITH 2,5 FURANDIONE, METAL SALTS and more particularly pertains to the use of 1-OCTADECENE, POLYMER WITH 2,5 FURANDIONE, METAL SALTS as Conducting Polymers. The Method of Using 1-OCTADECENE, POLYMER WITH 2,5 FURANDIONE, METAL SALTS to carry out various functions, is described herein.

Description of the Prior Art

Prior to 1988, all carbon-based polymers were exclusively classified as insulators. In fact, plastics have been used expensively in the electronics industry because of this very property. In 1979, Diaz and coworkers reported the conductive properties of polypyrrole. (Diaz, A. F., Kanazawa, K. K., and Gardini, G. P., Electrochemical Polymerization of Pyrrole, J Chem Soc Chem Commun, 635-6 (1979).) To date, numerous intrinsically conductive polymers or electroactive polymers have been developed. These polymers have versatile promising applications in the areas of electronic devices (Novak, P., Muller, K., Santhanam, K. S. V., and Haas, O., Electrochemically active polymers for rechargeable batteries, Chem Rev, 97, 207 (1997)), optical devices (Potember, R. S., Hoffman, R. C., Hu, H. S., Cocchiaro, J. E., Viands, C. A., Murphy, R. A., and Poehler, T. O., Conducting organics and polymers for electronic and optical devices, Polymer, 28, 574 (1987)), sensors (Nicholas, M., Fabre, B., and Simonet, J., Electrochemical Sensing of $F^-$ and $Cl^-$ with a Boric Ester-Functionalized Polypyrrole, J Electroanal Chem, 5091 (2001)), energy storage, medicine, and electrical infrastructure.

Intrinsically Conductive Polymers:

Intrinsically Conductive Polymers are polymeric organic compounds that exhibit the property of electrical conductivity. In general, these materials are either semiconductors or have metal conductivity. Conducting polymers have carbon backbones consisting of conjugated $sp^2$ hybridized carbon bonds. One valence electron associated with each of these $sp^2$ hybridized carbon atoms exists in a $p_z$ orbital orthogonally positioned relative to the three sigma bonds associated with the hybridized carbon atom. The electrons in these $p_z$ orbitals are termed delocalized and generally have high mobility when the material is "doped" by oxidation, a process that removes some of these delocalized electrons. Similarly, intrinsically conductive polymers can be created by the reduction of conjugated carbon backbones. In general, most conductive polymers are "doped" by oxidation to give "p-type" materials. This process is analogous to the doping of silicon semiconductors.

To date, these polymer preparations all suffer from the same drawbacks—poor processability and the lack of essential mechanical properties. In an attempt to address these limitations, efforts have been directed toward the production of composites of conducting polymer films and insulating polymers. For example, an insulating polymer, such as polycarbonate, is combined with a conducting polymer, such as polypyrrole, to produce conducting polymer composites that are conductive and have better mechanical functionality. (Wang, H. L., Toppare, L., and Fernandez, J. E., Conducting polymer blends: polythiophene and polypyrrole blends with polystyrene and poly(bisphenol A carbonate), Macromolecules, 23, 1053-9 (1990).)

Other insulating polymers used include poly(styrenesulphonate) (Otero, T. F., and Sansinena, J. M., Influence of synthesis conditions on polypyrrole-poly(styrenesulphonate) composite electroactivity, J Electroanal Chem, 412, 109-16 (1996)), poly(vinylchloride) (De Paoli, M. A., Waltman, R. J., Diaz, A. F., and Bargon, J, An electrically conductive plastic composite derived from polypyrrole and poly(vinylchloride), J Polym Sci Polym Chem Ed, 23, 1687-97 (1985)), nitrile rubber (Naoi, K., and Osaka, T., Highly enhanced anion doping-undoping process at the polypyrrole electrode of regulated morphology prepared with the aid of insulating NBR film, J Electrochem Soc Electrochem Sci Tech, 134, 2479-83 (1987)), polyimide (Iroh, J. O., and Levine, K., Electrochemical synthesis of polypyrrole/polyimide conducting composite using a polyamic acid precursor, Eur Polym J, 38, 1547-50 (2002)), and poly(vinyl alcohol) (Gangopadhyay, R., and De, A., Conducting polymer composites: novel materials for gas sensing. Sensors and Actuators B, 77, 326-9 (2001)). Other conducting polymers reported include polyaniline and polythiophene.

Energy storage devices have been reported that include an electrode composed of a conducting polymer and either a liquid or solid electrolyte. In solid state devices, a layer of electrolyte is sandwiched, either neet or impregnated in a matrix, between two electrodes. Performance of the storage devices is enhanced by electrochemically doping the conducting polymers with a dopant anion or cation. In these devices, the conducting polymer serves as the electronic conductor and the electrolyte matrix serves as the ionic conductor. The major drawback reported with these devices is the relatively low diffusion rate of the dopant ion into the polymer electrode, resulting in a high degree of internal resistance and a reduction in device performance.

Novel composites of an ionic conducting polymer and an electronic conducting polymer have also been reported (Berthier, C. M, Friend, R. H., Novel composites of an ionic conducting polymer and an electronic conducting polymer, U.S. Pat. No. 4,681,822.) These composites are composed of interpenetrating networks of a continuous electronic conducting material and a continuous ionic conducting material. Electronic conducting materials include polyacetylene, polyphenylene, polyphenyl diphenyl vinylene or a substituted polyacetylene, which are intimately mixed with a continuous ionic conducting material, defined as "a mixture of a complex of an ionic salt and a polymeric solvating agent such that the ionic conducting material has an increased melting point over its normal melting point." The ionic salts used were limited to polyatomic anions, such as $AsF_6^-$, $PF_6^-$, $BF_4^-$ and $Cl_4^-$, and alkali metal cations.

Additionally, in order to be effective, these ionic salts had to be mixed with a polymeric solvating agent, such as a polyalkylene oxide, capable of solvating the ionic salt. Additionally, the electronic conducting polymer must contain conjugated carbon-carbon double bonds capable of forming either "p-type" or "n-type" materials. The major advantage of these composites over the related conducting polymer/liquid-solid electrolyte devices is an increase in the ion diffusion rate of the dopant ion, and hence improved performance of the solid state energy storage device.

Nanoparticle Composites:

Numerous organic compound/metal nanoparticle composite conductive materials have been reported. Yang, et. at., reported the synthesis of polypyrrole/silver conducting nanotubes. (Yang, X., Li, L., Yan, F., Fabrication of Polypyrrole/Ag Composite Nanotubes via In Situ Reduction of $AgNO_3$ on Polypyrrole Nanotubes, Chemistry Letters, 39(2): 118 (2009).) Meftah et. al., reported the synthesis of nickel nanoparticle/polyaniline composite films and their use in electronics, electrocatalystics, and optoelectronics. (Meftah, A. M., Saion, E., Abd, M., Mohd, M. B., Zainuddin, H. B., Absorbance of Nickel Nanoparticles/Polyaniline Composite Films Prepared by Radiation Technique, Solid State Science and Technology, 17(2), 167-174 (2009).)

Buttry in U.S. Patent Application 2009/0272949A1 discloses a method of producing metal oxide nanoparticles encapsulated with conducting polymers that are suitable for use as lithium ion battery cathodes or as catalytic materials. (Buttry, D. A., Method for Producing Metal Oxide Nanoparticles Encapsulated with Conducting Polymers, United States Patent Application Publication US 2009/0272949A2, 2009). Holliday in US Patent Application 2010/0038599A1 discloses compounds comprised of at least one semiconductor and/or photon absorber covalently linked to a conjugated conductive polymer. (Holliday, B. J., Polymerizable Semiconductors, Polymers Thereof, and Methods of Making and Using Same, United States Patent Application Publication US 2010/0038599A1, 2010). In all cases, and as seen with intrinsically conductive polymers, the polymers reported in these nanocomposite systems all contained either conjugated double bond systems or electron systems delocalized over several conjugated carbon atoms.

Metal-Containing Polymers

In 1979, Dawans and Morel reported, in U.S. Pat. No. 4,150,067, the development of organometallic polymers consisting of a backbone of saturated carbon atoms complexed to transition metal atoms. In order to obtain these organometallic materials, the polymers had to contain fluororcarboxylic acid groups, and the transition metals required ligand stabilization. As these inventors stated " . . . there was an interest in the preparation of polymers including groups able to enhance the catalytic activity of the metal while maintaining said metal strongly bound to the polymeric carrier, in order to avoid that the catalytic complex be liberated in the medium during the reaction . . . . It has now been discovered that polymers containing the convenient fluorocarboxylic acid groups may be used as carriers for metal derivates and lead in particular to the formation of very active catalysts for various reactions." (Dawans, F., Morel, D., Metal-Containing Polymers, Their Manufacture and Use, U.S. Pat. No. 4,150,067 (1979).) Thus, these inventors taught away from the concept that carboxylic acid groups alone could sufficiently bind metals strongly to the polymeric carrier, thereby avoiding liberation during subsequent reactions.

Use of 1-Octadecene, Polymer with 2,5 Furandione in Conducting Polymers:

Poly(ethylene oxide) (PEO) based solid polymer electrolytes have been widely reported due to the observation that the ethylene oxide units provide for the efficient solvation of metal cations. (Armand, M. B. In Polymer Electrolytes Review; McCallum, J. R., Vincent, C., Eds.; Elsevier Applied Science: London, 1987; Vol. 1, p 1.; Gray, F. M. Polymer Electrolytes; The Royal Society of Chemistry: Cambridge, (1997). Due to the high crystallization aptitude of PEO, low conductivity of the salt complexes is observed at room temperature, thereby limiting its use in solid state electrochemical devices. To overcome this deficiency, poly (ethylene glycol) monomethyl ether (PEGME) has been grafted into the side chain of polymers such as polyacrylate and maleic anhydride copolymers. Tang and coworkers describe the synthesis and properties of multifunctional comb-like polymer electrolytes synthesized using poly(ethylene glycol) monomethyl ether (PEGME) as the metal-binding side chain and poly(maleic anhydride-alt-1-octadecene) (PMAO) as the backbone. (Tang, Z-l., Qi, L., Gao, G-t., Sun, M., Dong, S-j. Synthesis and Properties of Multifunctional Comblike Polymer Electrolytes, Journal of Functional Polymers, 21(1): 36-43, (2008).)

Saad and coworkers reported on the electrical properties of poly(vinyl chloride) (PVC) compositions containing PVC, a polar plasticizer, and a copolymer of 1-octadecene and maleic anhydride. (Saad, A. L. G., Hassan, A. M., Gad, E. A. M. Electrical Properties of Poly(vinyl chloride) Compositions, Journal of Applied Polymer Science, 49(10): 1725-31 (1993).) Electrically conductive polymer—filler composites comprised of a polycarbonate and an acrylonitrile-butadiene-styrene copolymer wherein the ratio of the polycarbonate and the acrylonitrile-butadiene-styrene copolymer ranged from 4 to 6 to 6 to 4 have been reported by Kim and coworkers. (Kim, W. and Lee, Y., Electrically Conductive Polymer/Filler Composites, International Patent Application No.: PCT/KR2011/010189, Publication Number WO20122012115344.)

Additionally, polymeric Langmuir-Blodgett films containing a metal binding ligand, such as imidazole, formed from polymers obtained by the reaction of histamine with poly(maleic anhydride-alt-1-octadecene) have been reported. (Jeong, H., Lee, B-J., Cho, W. J., Ha, C-S., Polymeric Langmuir-Blodgett Films Containing Imidazole-coordinated Metal Complexes, Polymer, 41(14): 5525-5529 (2000); Jung, S-B., Yoo, S-Y., Kwon, Y-S., Characterization of Metal-ion Complexes of IMI-O Polymer LB Films, J. Kor. Phys. Soc., 37(4): 378-308 (2000); Yoo, S-Y., Shin, H-K., Jeong, H., Park, J-C., Kwon, Y-S., Structure Analysis of Langmuir and Langmuir-Blodgett Films with Metal Complexes, Mol. Cryst. and Liq. Cryst., 337:357-360 (1999).) Similar films using polymers composed of other nitrogen-containing metal-binding ligands, such as 4-aminopyridine, 4-aminomethylpyridine, or polyimide, have also been reported. (Nagel, J., Ulrich, O., Langmuir-Blodgett Layers from Polymer-metal Complexes: Behavior of Monolayers and Preparation of Multilayers, Polymer, 36(2):381-386 (1995); Bruckner-Lea, C., Petelenz, D., Janata, Use of Poly(octadec-1-ene-maleic anhydride) for Interfacing Bilayer Membrane Supports in Sensor Applications, J., Microchimica Acta 100:169-185 (1990).)

Hydrophobicity and Acid Number:

In reference to polymeric materials containing carboxylic acid functional groups, acid number is defined as the number of milligrams of potassium hydroxide required to neutralize 1 gram of the polymer. Thus, it is representative of the molar ratio of carboxylic acid groups to polymer and reflects the polar acid content of the polymers or resins. The greater the acid value, the greater the number of carboxylic acid groups, and the greater the polarity of the molecule.

In reference to Poly(octadec-1-ene-maleic anhydride), Suzuki, Y in U.S. Pat. No. 5,298,568 described a modified olefin resin which can be dissolved in water by neutralization with an alkali and has an acid value of at least 30. These resins were obtained from "an α-olefin having at leas 6 carbon atoms and maleic anhydride with at least one modifier have at least one functional group selected from the class consisting of hydroxyl, amino, aziridinyl and mercapto groups". Further, he teaches that in order to obtain the desired water solubility, the "acid value of the modified olefin resin is at least 30, preferably 80 or more. A modified resin having an acid value less than 30 hardly shows alkali solubility and water compatibility".

Suzuki teaches that resins with low acid numbers (less than 30) are water insoluble, while those greater than 30 are water soluble. Suzuki teaches away from the polymers described in the present invention, as the polymers described in the present invention are water insoluble and hydrophobic with acid numbers greater than 100. The resins disclosed by Suzuki are also limited in the metals they are capable of binding. Suzuki discloses that his resins bind transition metal compounds having a valence of at least 2. The polymers described in the present invention are capable of binding metal compounds having a valence of at least 1. Koide, et al., in Japanese Patent Number 05-202234 describe copolymer resins composed of an $\alpha,\beta$-ethylenically unsaturated monomer with an ethylenically unsaturated dibasic acid or its anhydride that are chelating agents. The resins described by Koide, having an acid value of 20 to 100, are hydrophobic, while those with greater acid values are hydrophilic. The polymers detailed in the present invention are water-insoluble, hydrophobic chelating agents having acid numbers greater than 100. Additionally, the agents described by Koide chelate sodium, potassium, and magnesium. The polymers disclosed in the present invention do not bind sodium, potassium, or magnesium. Thus, Koide teaches away from ethylene-based, water-insoluble, hydrophobic polymers having acid numbers greater than 100 that are able to bind metals.

Limitations of Current Conducting Polymers:

Presently, all conducting polymers suffer from one or more of the following limitations: poor processability, the lack of essential mechanical properties, and a high degree of internal resistance and limited device performance with polymers containing dopant ions. Further, all conducting polymers structurally require either conjugated multiple bond systems or fluorocarboxylic acid functional groups and ligand-stabilized transition metals. Thus, the prior art teaches away from conducting polymers, such as 1-octadecene, polymer with 2,5 furandione, metal salts, that do not contain conjugated multiple bond systems, fluorocarboxylic acid functional groups, or ligand-stabilized transition metals.

Further, the use of 1-octadecene, polymer with 2,5 furandione as a component in conducting polymers has been limited to its use solely as a backbone, or support. These observations indicate that the use of 1-octadecene, polymer with 2,5 furandione as both a backbone or support and the metal binding functional group was not anticipated or obvious to those schooled in the art.

In summary, the characteristics of the polymer described herein are not predicted in the literature, as conductivity is obtained without the requirements for either a conjugated multiple bond system or fluororcarboxylic acid functional groups and ligand-stabilized transition metals. As such, the use of the polymer as a conductor in the manner described is unexpected, constitutes a new and unexpected use for the polymer, and functions in a new, unanticipated manner.

While these compounds disclosed in the prior art fulfill their respective, particular objectives and requirements, the aforementioned patents and prior art do not describe the Conducting Polymers, 1-Octadecene, Polymer with 2,5 Furandione, Metal Salts that allow the use of conducting polymers without the need for conjugated multiple bond systems or fluorocarboxylic acid functional groups, ligand-stabilized transition metals, or metal binding homopolymer components.

In this respect, the Conducting Polymers, 1-Octadecene, Polymer with 2,5 Furandione, Metal Salts, according to the present invention substantially depart from the conventional concepts and compounds described in the prior art, and in doing so provide unique conductive polymer compounds capable of electron transmission.

Therefore, it can be appreciated that there exists a continuing need for new and improved Conducting Polymers, and 1-Octadecene, Polymer with 2,5 Furandione, Metal Salts, which can be used for electron transmission. In this regard, the present invention substantially fulfills this need.

SUMMARY OF THE INVENTION

1-Octadecene, Polymer With 2,5 Furandione, Metal Salts, prepared from 1-Octadecene, Polymer with 2,5 Furandione, Sodium Salt, as previously described (Laurino, J. P., U.S. Pat. No. 7,964,688) or by other preparative means as would be evident to those skilled in the art, possess novel conductive polymer characteristics. The characteristics include, but are not limited to, conductivities of 4 S/cm to 200 S/cm or more, depending upon the concentration and nature of the metal bound, conductivities proportional to the amount of metal bound to the polymer, the ability to bind metals having a +1, +2, +3, +4, or +5 valence charge to the polymer, and the ability to bind two or more different metals to separate binding sites on the polymer.

Essential Characteristics of the Polymers:

The polymers, as herein described, contain numerous carboxylate groups directly bound to the polymer backbone that provide the hydrophilic metal-binding characteristics. The polymers also contain a water insoluble hydrophobic aliphatic polymer backbone. These polymers provide specific, selective, and fast complexation of metal ions, thereby producing conductive polymer materials.

Comparison of Conductivities:

The conductivities of various conductive polymers are given in the table below:

| POLYMER | CONDUCTIVITY (S/cm) |
|---|---|
| Polyaniline | 10* |
| Poly(p-phenylene vinylene) | 1* |
| Polythiophene | 200* |
| Polypyrrole | 600* |
| Poly-p-phenylene sulphide | 20* |
| 1-Octadecene, Polymer With 2,5 Furandione, Iron (III) Salt | 250 |
| 1-Octadecene, Polymer With 2,5 Furandione, Copper (II) Salt | 20 |
| 1-Octadecene, Polymer With 2,5 Furandione, Nickel (II) Salts | 5 |
| 1-Octadecene, Polymer With 2,5 Furandione, Cadmium (II) Salts | 5 |
| 1-Octadecene, Polymer With 2,5 Furandione, Zinc (II) Salts | 20 |

*As reported in Kumar, D., Sharma, R. C., Eur. Polym. J., 34(8): 1053-1060 (1998)

The conductivity readings of the 1-Octadecene, Polymer With 2,5 Furandione, Metal Salts were obtained using the lowest concentration of metal salt solution for the conducting polymer preparation. Increasing conductivities were obtained when metal salt solutions of increasing concentrations were used for the preparation of the conducting 1-octadecene, polymer with 2,5 furandione, metal salts.

The polymers, herein described, have several potential uses that are beneficial. The polymers can be used as a conducting means of electrical energy. The term "conducting means" is at least one structure from the group of structures, which are used for the conduction of electricity, which includes films, wires, electrodes, nanowires, fibers, filaments, inks, printed circuits and printed products.

The polymer can also be used as an "electronic component means," which is at least one member of the group of electronic components which includes electrolytic capacitors, switches, injection molded products, temperature gauges, solenoids, photovoltaic cells, displays, electric glues, energy storage cells including batteries, semiconductors, biosensors, and devices which are used to measure electrical impedance. When used in energy storage cells, it is understood that at least one cell of the energy storage cell utilizes the polymer herein described. The energy storage cells are comprised of at least two electrodes associated with at least one cell.

Additionally, since the role of transition metal ions as disinfectants of bacteria and viruses has been previously reported (McDevitt, C. A., Ogunniyi, A. D., Valkov, E., Lawrence, M. C., Kobe, B., McEwan, A. G., Paton, J. C., A Molecular Mechanism for Bacterial Susceptibility to Zinc, PLoS Pathog. 7(11) 2011; Thurman, R. B., Gerba, C. P., Bitton, G., The Molecular Mechanisms of Copper and Silver Ion Disinfection of Bacteria and Viruses, Crit. Rev. in Environ. Control. 18(4):295-315 (1989); Molteni, C., Abicht, H. K., Solioz, M., Killing of Bacteria by Copper Surfaces Involves Dissolved Copper, Appl. Environ. Microbiol., 76(12): 4099-4101 (2010)), these unique metal-bonded polymers can serve as components of antimicrobial and antiviral "barrier means", which is at least one of a group of barrier means which includes bandages, gowns, gloves, sutures, surgical draping, clothing, bedding, and barrier items including sheets, screens, bags, masks, head covers, air filters, room dividers, flooring, and injection molded plastics.

Lead has long been recognized as a highly effective material in providing a protection barrier from various sources of radiation (A Guide to the Use of Lead for Radiation Shielding, A publication of the Lead Industries Association, Inc., 292 Madison Avenue, New York, N.Y.). As such, these unique lead-bonded and other metal-bonded polymers can serve as components of "radiation barrier means", which is at least one of the group of radiation barriers which includes clothing, gloves, screens, room partitions, draping, sheets, bedding, gowns, bags, masks, head covers, air filters, room dividers, flooring, and injection molded plastics.

Similarly, these polymers can also be used as an "anti-fouling means", which is at least one of the group of anti-fouling agents which includes anti-mold agents, anti-mildew agents, anti-algal agents, and anti-fouling agents. (Kheybari, S., Samadi, N., Hosseini, S. V., Fazeli, A., Fazeli, M. R., Synthesis and Antimicrobial Effects of Silver Nanoparticles Produced by Chemical Reduction Method, Daru, 18(3): 168-172 (2010); Schiff, K., Diehl, D., Valkirs, A., Copper Emissions from Antifouling Paint on Recreational Vehicles, Marine Pollution Bulletin, 48(3-4):371-377 (2004)).

These polymers can be used in the preparation of "photographic means", which is at least one of the group of photographic materials which includes photosensitive materials containing polymer chelated metals, such as silver, platinum, palladium, and gold. (Arentz, D., Photography in Platinum and Palladium, Platinum Metals Review, 49(4): 190-195 (2005); Sun, Y., Xia, Y., Shape-Controlled Synthesis of Gold and Solver Nanoparticles, Science, 298, 2176 (2002)).

These polymers can also be used in the preparation of "treatment means", which is at least one of the group of treatments which includes anti-cancer treatments, anti-inflammatory treatments, anti-infective treatments, anti-diabetic pharmaceutical compounds and cosmetic preparations. They can also be used in the preparation of dietary supplements, diagnostic agents, and dental filings and implants. (Warra, A. A., Transition Metal Complexes and Their Application in Drugs and Cosmetics—A Review, J. Chem. Pharm. Res., 3(4): 951-958 (2011)).

These polymers can also be used in the preparation of chelated fertilizers and inorganic pesticides, or "fertilizer means" and "pesticide means", respectively. A fertilizer means is at least one of the group of fertilizer micronutrients which includes iron, manganese, zinc, copper, and nickel. Chelated fertilizers have been developed to increase the utilization efficiency of micronutrients, such as iron, manganese, zinc, copper, and nickel. Since these micronutrients are easily oxidized or precipitated in soil, the utilization of the unchelated metal is not very efficient (Liu, G., Hanlon, E., Li, Y. Understanding and Applying Chelated Fertilizers Effectively Based on Soil pH., Document HS 1208, University of Florida, Horticultural Sciences Department, Florida Cooperative Extension Service, Institute of Food and Agricultural Sciences, November 2012; Sekhon, B. S., Chelates for Micronutrient Nutrition among Crops. Resonance, 8(7): 46-53 (2003)).

Copper, cadmium, cobalt, nickel, lead, zinc, iron, manganese, and other metals are also components of common pesticides. (Gimeno-Garcia, E, Andreu, V., Boluda, R., Heavy Metals Incidence in the Application of Inorganic Fertilizers and Pesticides to Rice Farming Soils, Environmental Pollution, 92(1): 19-25 (1996)). A pesticide means is at least one of the group of pesticide components which includes copper, cadmium, cobalt, nickel, lead, zinc, iron, and manganese.

These polymers can also be used as a "catalyst means". Numerous investigators have reported on the use of platinum-polyacid, palladium polyacid, rhodium metal-polymer, and other transition metal-polymer catalysts.

When used herein the term "catalyst means" is at least one of the group of polymer catalysts that includes a transition metal (Mayer, A. B. R., Mark, J. E., and Hausner, S. N. Collodial platinum-polyacid nanocatalyst systems), or a non transition metal. The non-transition Metals being Aluminum and Lead. The transition Metals being Scandium, Titanium, Vanadium, Chromium, Manganese, Iron, Cobalt, Nickel, Copper, Zinc, Yttrium, Zirconium, Niobium, Molybdenum, Technetium, Ruthenium, Rhodium, Palladium, Silver, Cadmium, Hafnium, Tantalum, Tungsten, Osmium, Iridium, Platinum, Gold, Mercury, Lutentium, and Rhenium.

(Angew. Makromol. Chem., 259:45-53 (1998); Mayer, A. B. R., Mark, J. E., and Hausner, S. N. Palladium nanocatalysts protected by polyacids. J. Appl. Poly. Sci., 70(6):1209-1219 (1998); Banavali, R., Deetz, M. J., and Schultz, A. K. Transition Metal Catalysts, in The Power of Functional Resins in Organic Synthesis (eds. J. Tulla-Puche and F. Albericio), Wiley-VCH Verlag GmbH & Co. KGaA, Weinheim, Germany (2009).)

In view of the foregoing disadvantages inherent in the known types of conducting polymers now present in the prior art, the present invention provides improved conducting polymers, 1-Octadecene, Polymer with 2,5 Furandione, Metal Salts. As such, the general purpose of the present invention, which will be described subsequently in greater detail, is to provide a new conducting polymer which has all the advantages of the prior art and none of the disadvantages.

To attain this, the present invention essentially comprises a conducing polymer comprising an aliphatic polymer backbone. The backbone is a hydrophobic, aliphatic, saturated carbon atom structure. There are two metal carboxylate groups per repeating unit that are directly bound to the polymer backbone.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least on embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose and descriptions and should not be regarded as limiting.

As such, those skilled in the art will appreciate that the conception, upon which this disclosure is based, may readily be utilized as a basis for the designing of other formulations, and methods for carrying out the several purposes of the present invention. It is important, therefore, that the claims be regarded as including such equivalent formulations insofar as they do not depart from the spirit and scope of the present invention.

It is therefore an object of the present invention to provide new and improved conducting polymers, 1-Octadecene, Polymer with 2,5 Furandione, Metal Salts, and Method of Use of conducting polymers, 1-Octadecene, Polymer with 2,5 Furandione, Metal Salts which has all of the advantages of the prior art conducting polymers and none of the disadvantages.

It is another object of the present invention to provide new and improved new and improved conducting polymers, 1-Octadecene, Polymer with 2,5 Furandione, Metal Salts, and Method of Use of conducting polymers, 1-Octadecene, Polymer with 2,5 Furandione, Metal Salts which may be easily and efficiently manufactured and marketed.

It is a further object of the present invention to provide new and improved new and improved conducting polymers, 1-Octadecene, Polymer with 2,5 Furandione, Metal Salts, and Method of Use of conducting polymers, 1-Octadecene, Polymer with 2,5 Furandione, Metal Salts which are easily reproduced.

An even further objective of the present invention is to provide new and improved new and improved conducting polymers, 1-Octadecene, Polymer with 2,5 Furandione, Metal Salts, and Method of Use of conducting polymers, 1-Octadecene, Polymer with 2,5 Furandione, Metal Salts which is susceptible to a low cost of manufacture with regard to both materials and labor, and which accordingly is then susceptible to low prices of sale to the consuming public, thereby making such new and improved conducting polymers, 1-Octadecene, Polymer with 2,5 Furandione, Metal Salts, and Method of Use of conducting polymers, 1-Octadecene, Polymer with 2,5 Furandione, Metal Salts economically available to the buying public.

Even still another object of the present invention is to provide new and improved conducting polymers, 1-Octadecene, Polymer with 2,5 Furandione, Metal Salts, and Method of Use of conducting polymers, 1-Octadecene, Polymer with 2,5 Furandione, Metal Salts for use in energy storage and transmission.

Lastly, it is an object of the present invention to provide new and improved conducting polymers, 1-Octadecene, Polymer with 2,5 Furandione, Metal Salts, and Method of Use of conducting polymers, 1-Octadecene, Polymer with 2,5 Furandione, Metal Salts for use as anti-bacterial, anti-fungal, anti-mold, anti-viral, anti-mildew, anti-algal, and anti-fouling agents.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
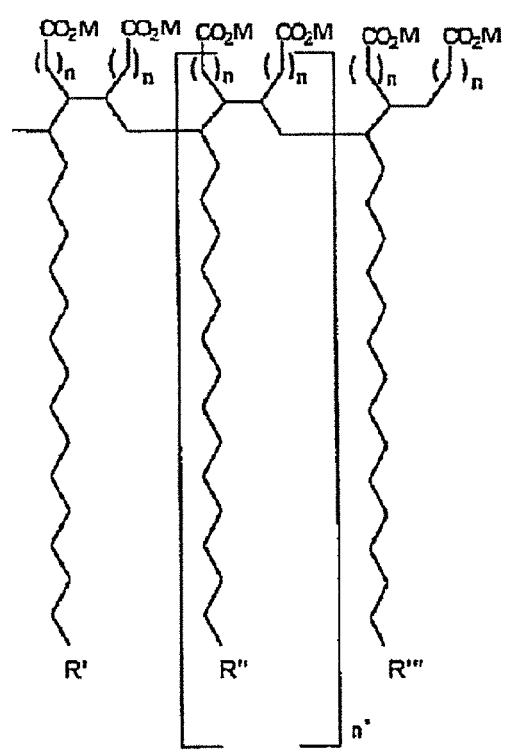
FIG. 1 is a drawing of the compound, showing the pertinent structure and formula, wherein M is a metal ion, R', R", and R'" are one of the structures from the group of structures which include alkyl, alkenyl, and aryl structures; n is an integer number, including 0, of methylene groups; and n' is an integer number of monomer units.

With reference now to the drawings, and in particular to FIG. 1 thereof, the preferred embodiment of the new and improved conducting polymers, 1-Octadecene, Polymer with 2,5-Furandione, Metal Salts embodying the principles and concepts of the present invention will be described. Simplistically stated, the polymer herein described comprises a plurality of reactive groups, being carboxylates or carboxylic acid groups bound to valent metal ions. The term "valent metal ion" refers to a member of the group of valent metal ions which includes monovalent metal ions, divalent metal ions, trivalent metal ions, tetravalent metal ions, and pentavalent metal ions. The reactive groups are directly bonded to the carbon backbone. It is understood to those skilled in the art that a monovalent metal ion is capable of binding to one reactive group, a divalent metal ion is capable of binding to two reactive groups, a trivalent metal ion is capable of binding to three reactive groups, a tetravalent metal ion is capable of binding to four reactive groups, and a pentavalent metal ion is capable of binding to five reactive groups.

It should be understood that reference to "valent metal ions", when used to refer to a monovalent ion, means that the bond is with at least one reactive group. Likewise, reference to valent metal ions, when used to refer to a divalent metal ion, means that the bond is with at least two reactive groups. The term valent metal ions, when used to refer to a trivalent ion, means that the bond is with at least three reactive groups. The term valent metal ions, when used to refer to a tetravalent metal ion, means that the bond is with at least four reactive groups. The term valent metal ions, when used to refer to a pentavalent ion, means that the bond is with at least five reactive groups.

Figure 2:
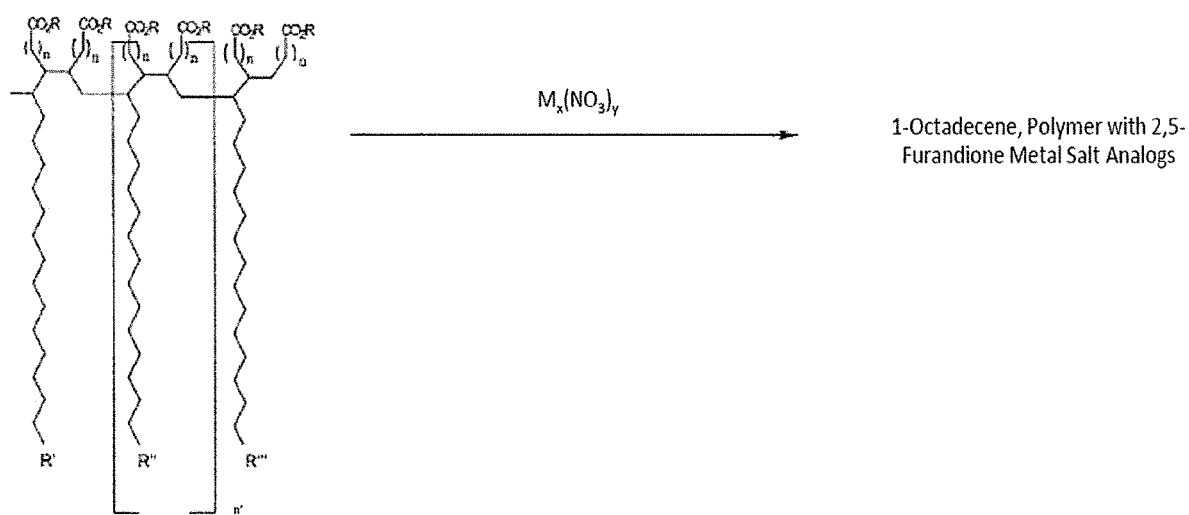
FIG. 2 is a drawing of a synthetic route for 1-Octadecene, polymer with 2,5-furandione metal salt analogs, wherein M is a metal, R is H, R', R", and R'" are one of the structures from the group of structures which include alkyl, alkenyl, and aryl structures; n is an integer number, including 0, of methylene groups; n' is an integer number of monomer units, and x and y represent the number of metal and polyatomic ions, respectively.

The initial, or primary component, for the synthesis, is produced by a process that is described and disclosed in U.S. Pat. No. 7,964,688, issued to J. P. Laurino, entitled "Chelating compound, and method of use of, poly(1-octadecyl-butanedioate) and the corresponding acid, poly(1-octadecyl-butane dioic acid). The conducting polymers, 1-Octadecene, Polymer with 2,5-Furandione, Metal Salts, may be prepared from the polycarboxylate as shown in FIG. 2 and as follows:

10 grams of the polycarboxylate is added to a solution of the metal nitrate at room temperature. The reaction mixture is allowed to react for 5 minutes, vacuum filtered, and the solid conducting polymer dried.

There are other methods to produce the conducing polymers, 1-Octadecene, Polymer with 2,5-Furandione, Metal Salts. One method is to use the corresponding polyester. Subsequent hydrolysis of the polyester would produce the polycarboxylate, which could then be reacted with the metal nitrate solution. Additionally, other soluble metal salts can be used to prepare the conducting polymer from the polycarboxylate. These reaction schemes would be obvious to someone skilled in the art of organic synthesis or polymer synthesis.

It should also be noted that the polycarboxylate has two different binding site populations. In FIG. 2. if n=0, the reactive groups in the repeating unit are two carbons apart while the reactive groups between the repeating units are four carbons apart. It is readily apparent that these two binding sites have different three-dimensional geometries. Additionally, the reactive groups must be attached to the backbone and do not have to be attached to adjacent carbon atoms. Therefore, it is possible that the polymer chain(s), being flexible, is (are) able to surround the metal, thereby enhancing binding to the metal ions.

FIGURES

FIG. 1 shows the pertinent structure and formula of the conducing polymers, 1-Octadecene, Polymer with 2,5-Furandione, Metal Salts. FIG. 1 is the first configuration of the compound.

FIG. 2 shows a synthetic route for conducting polymers, 1-Octadecene, polymer with 2,5-furandione metal salt analogs. Given the measured conductivity of the conducting polymers, 1-Octadecene, polymer with 2,5-furandione metal salt analogs, the polymers described herein have several potential uses that are beneficial. The polymers can be used as a conducting means which is at least one of the conductors from the group of conductors which includes films, wires, electrodes, nanowires, fibers, filaments, inks, printed circuits, and printed products.

These polymers can also be used as electrical component means, which is at least one of the group of electrical components which includes electrolytic capacitors, switches, injection molded products, temperature gauges, solenoids, photovoltaic cells, displays, electric glues, energy storage cells, semiconductors, biosensors, and electrical impedance sensors.

Additionally, these metal-bonded polymers can serve as components of antimicrobial and antiviral barrier means, which is at least one of the group of antimicrobial and antiviral barriers which includes bandages, gowns, gloves, sutures, surgical draping, clothing, bedding, and barrier items including sheets, screens, bags, masks, head covers, air filters, room dividers, flooring, and injection molded plastics.

These metal-bonded polymers can also serve as a radiation barrier means, which is at least one of the group of radiation barriers which includes clothing, gloves, screens, room partitions, draping, sheets, bedding, gowns, bags, masks, head covers, air filters, room dividers, flooring, and injection molded plastics. Similarly, these metal-bonded polymers can also be used as an anti-fouling means, which is at least one of the anti-fouling agents which includes anti-mold agents, anti-mildew agents, anti-algal agents, and anti-fouling agents.

These polymers can also be used as an anti-infective means, in the preparation of anti-cancer, anti-inflammatory, anti-infective, and anti-diabetic pharmaceutical compounds and cosmetic preparations. An Anti-infective means is at least one of the group of anti-infective agents which includes anti-cancer, anti-inflammatory, anti-infective, and anti-diabetic pharmaceutical compounds and cosmetic preparations.

These polymers can also be used in the preparation of photographic means which is at least one of the group of photographic materials which includes photosensitive materials containing polymer-chelated metals.

These polymers can also be used in the preparation of "treatment means", which is one of a group of treatments which includes anti-cancer treatments, anti-inflammatory treatments, anti-infective treatments, disinfectants, anti-diabetic pharmaceutical compounds and cosmetic preparations. (Warra, A. A., Transition Metal Complexes and Their Application in Drugs and Cosmetics—A Review, J. Chem. Pharm. Res., 3(4): 951-958 (2011)). They can also be used in the preparation of dietary supplements, diagnostic agents, and dental filings and implants. Additionally, these polymers can also be used in the preparation of fertilizer means and pesticide means.

A fertilizer means is at least one of the group of fertilizer micronutrients which includes iron, manganese, zinc, copper, and nickel.

A pesticide means is at least one of the group of pesticide components which includes copper, cadmium, cobalt, nickel, lead, zinc, iron, and manganese.

Lastly, these polymers can also be used as a "catalyst means". A catalyst means is at least one of the group of polymer catalysts that includes a transition metal or a non-transition metal.

The non-transition Metals are Aluminum and Lead. The transition Metals are Scandium, Titanium, Vanadium, Chromium, Manganese, Iron, Cobalt, Nickel, Copper, Zinc, Yttrium, Zirconium, Niobium, Molybdenum, Technetium, Ruthenium, Rhodium, Palladium, Silver, Cadmium, Hafnium, Tantalum, Tungsten, Osmium, Iridium, Platinum, Gold, Mercury, Lutentium, and Rhenium.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function, and manner of operation, assembly and use, are deemed readily apparent and obvious to one skilled in the art, and all equivalent relationships to those illustrated in the drawings and described in the specifications are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An electron conducting polymer consisting of a water-insoluble polycarboxylate polymer complex consisting of the chemical structure:

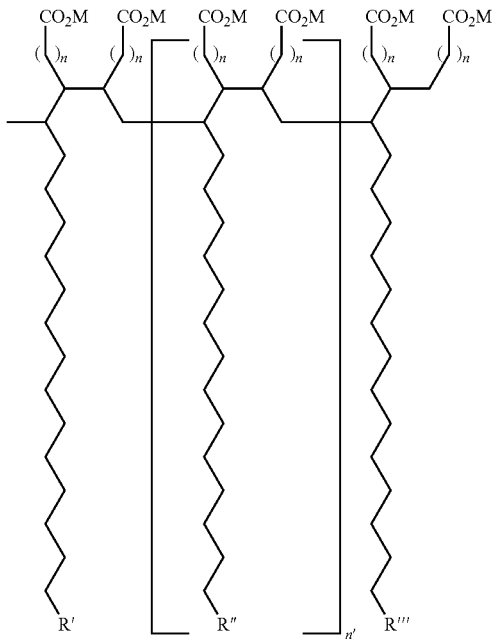

having an acid number greater than 100, wherein the electron conducting polycarboxylate polymer in the formula is the result of a corresponding water insoluble polycarboxylate polymer being reacted with an at least one metal ion wherein the at least one metal ion is bound to the water insoluble polycarboxylate polymer with the at least one metal ion being designated as M in the formula above, wherein at least one of the metal ions is bonded to an at least one carboxylate group of the water insoluble polycarboxylate polymer thereby forming the complex shown in the above formula, wherein the chemical structure of the attached groups being R', R", and R'" are each one of the structures selected from the group of structures which consists of alkyl, alkenyl, and aryl structures, wherein n is an integer number of methylene groups with the integer number including 0, and n' is an integer number of monomer units, wherein the metal ions are at least one of the group of metal ions of the metals which consists of a non transition metal being aluminum, and the transition metals being Scandium and Titanium and Vanadium and Chromium and Manganese and Iron and Cobalt and Nickel and Copper, and Zinc and Yttrium and Zirconium and Niobium and Molybdenum and Technetium and Ruthenium and Rhodium and Palladium and Silver, and Cadmium and Hafnium and Tantalum and Tungsten and Osmium and Iridium and Platinum and Gold and Mercury and Lutetium and Rhenium, with the Copper polymer complex forming an exclusively electron conducting complex.

2. The electron conducting polymer in claim 1 wherein the electron conducting polymer is used as a structured conducting means for the conduction of electricity.

* * * * *